US00PP20169P2

(12) United States Plant Patent
Stewart

(10) Patent No.: US PP20,169 P2
(45) Date of Patent: Jul. 7, 2009

(54) ***ANIGOZANTHOS* HYBRID PLANT NAMED 'RAMBODIAM'**

(50) Latin Name: *Anigozanthos hybrid*
Varietal Denomination: Rambodiam

(75) Inventor: Ian Angus Stewart, Somersby (AU)

(73) Assignee: Ramm Botanicals Holdings Pty., Ltd., Tuggerah, NSW (AU)

( * ) Notice: Subject to any disclaimer, the term of this patent is extended or adjusted under 35 U.S.C. 154(b) by 0 days.

(21) Appl. No.: 12/214,112

(22) Filed: Jun. 17, 2008

(51) Int. Cl.
*A01H 5/00* (2006.01)

(52) U.S. Cl. ..... Plt./362

(58) Field of Classification Search ..... Plt./362
See application file for complete search history.

(56) References Cited

PUBLICATIONS

Australian Plant Breeders" Rights Application No. 2008/118 filed Apr. 30, 2008, Application was not published by the time this IDS was prepared.

*Primary Examiner*—Annette H Para
(74) *Attorney, Agent, or Firm*—Audrey Charles

(57) ABSTRACT

'Rambodiam' is a distinctive variety of *Anigozanthos* hybrid which is characterized by the combination of its short plant height with an upright growth habit and an erect leaf attitude, large number of flowers per inflorescence and predominantly white-colored flowers.

1 Drawing Sheet

Latin name of the genus and species: *Anigozanthos* hybrid.
Variety denomination: 'Rambodiam'.

BACKGROUND OF THE INVENTION

The present invention relates to a new and distinct perennial variety of *Anigozanthos* hybrid, which has been given the variety denomination of 'Rambodiam'. Its market class is that of an ornamental plant. 'Rambodiam' is intended for use in landscaping and as a decorative plant.

The *Anigozanthos* hybrid variety 'Rambodiam' was the result of a spontaneous mutation of *Anigozanthos* hybrid 'Bush Pearl' in 2004 in Tuggerah, New South Wales, Australia. 'Rambodiam' was identified from a group of in vitro propagated plants of 'Bush Pearl' as a single whole plant mutation. 'Rambodiam' was observed to have a unique flower color consisting of a predominantly white perianth tube color whereas the normal color of 'Bush Pearl' is pink. The inventive variety was finally selected in July, 2004 based on its unique flowering traits. 'Rambodiam' was isolated and subsequently propagated in vitro during 2004 through 2005. Resultant plants were tested in 14 cm pots and in the ground during 2005 through 2007.

Asexual reproduction of the new cultivar by in vitro propagation of micro-plants since 2004 in Tuggerah, New South Wales, Australia has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Rambodiam' as a new and distinct cultivar of *Anigozanthos* hybrid plant:

1. Short plant height with an upright growth habit;
2. Erect leaf attitude;

3. Large number of flowers per inflorescence; and
4. Predominantly white-colored flowers.

Plants of the new cultivar differ from plants of the parent primarily in inflorescence color. 'Rambodiam' has the predominant color of the perianth tube as white whereas the parent has a pink predominant perianth tube color. The combination of short plant height with an upright growth habit and an erect leaf attitude, large number of flowers per inflorescence and a predominantly white colored perianth tube and ovary makes 'Rambodiam' a desirable ornamental plant suited for mass production for pot and landscape use. 'Rambodiam' is the first *Anigozanthos* hybrid with a predominantly white flower color.

Of the many commercially available *Anigozanthos* cultivars, the most similar in comparison to the new cultivar is the parent cultivar 'Bush Pearl', not patented. However, in side by side comparisons, conducted in Tuggerah, New South Wales, Australia plants of the new cultivar differ from plants of 'Bush Pearl' in at least the following characteristics:

1. 'Rambodiam' has a predominantly white-colored perianth tube whereas 'Bush Pearl' has a predominantly pink-colored perianth tube;
2. 'Rambodiam' has a predominantly white-colored ovary which may produce a slightly pink blush in some environments whereas 'Bush Pearl' has a predominantly pink-colored ovary; and
3. 'Rambodiam' has white-colored hairs on the pedicel corresponding to white (NN155B) with tips of these hairs colored red-purple (ranging from 59C to 59D) whereas 'Bush Pearl' has hairs colored red-purple (ranging from 67A to 67B).

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Rambodiam'.

DETAILED BOTANICAL DESCRIPTION

Figure 1:
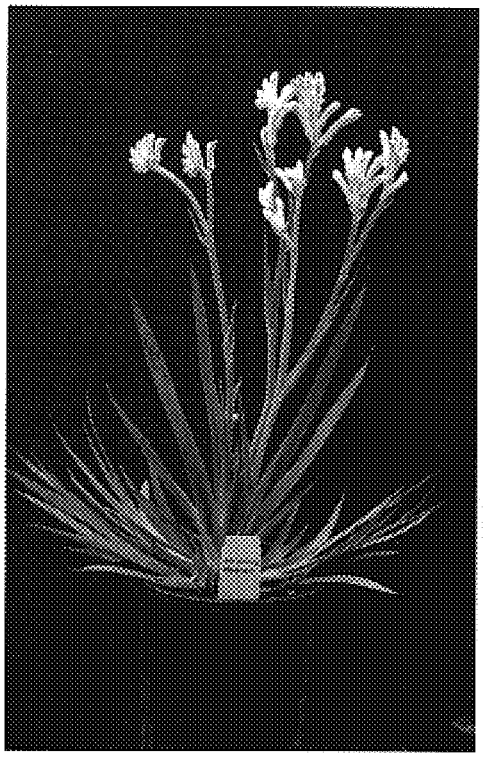
FIG. 1 illustrates a 'Rambodiam' plant in a 14 cm pot grown for approximately 14 weeks in a greenhouse environment.
Figure 2:
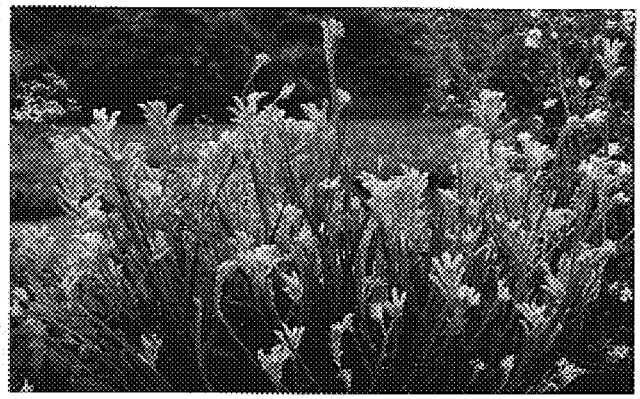
FIG. 2 illustrates a 'Rambodiam' plant in the landscape environment grown for approximately 40 weeks.
Figure 3:
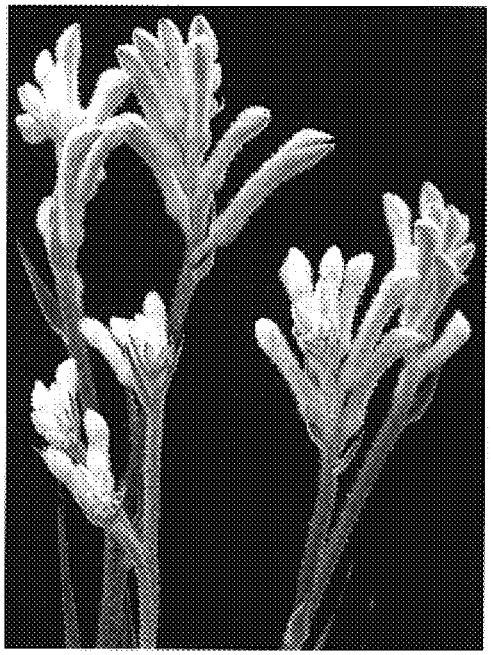
FIG. 3 illustrates a 'Rambodiam' inflorescence branching pattern.
Figure 4:
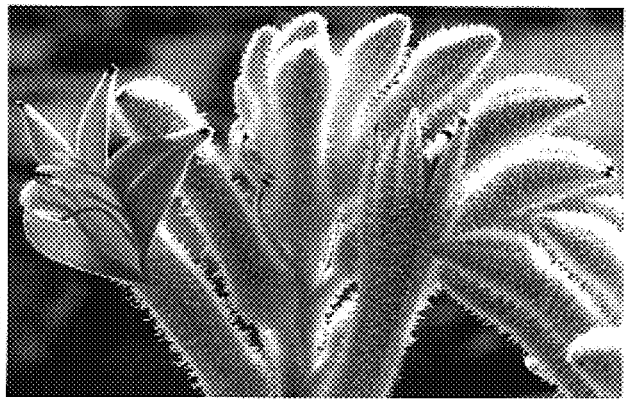
FIG. 4 illustrates 'Rambodiam' flowers within the inflorescence showing flower and hair detail.

The following is a detailed botanical description of a new and distinct variety of an *Anigozanthos* hybrid ornamental plant known as 'Rambodiam'. Plant observations were made on plants grown in Tuggerah, New South Wales, Australia. Unless indicated otherwise, the descriptions disclosed herein are based upon observations made from January 2008 of mature 'Rambodiam' plants grown in nursery pots in greenhouse and outdoor growing areas with day temperature ranging from 25° C. to 27° C., night temperatures ranging from 6° C. to 8° C., and light levels ranging from 6 to 8 klux. Plants were grown for about 24 weeks with one plant per 14 cm container. Those skilled in the art will appreciate that certain characteristics will vary with older or, conversely, younger plants. 'Rambodiam' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Color Chart, of The Royal Horticultural Society, London, 2007 edition.

Botanical classification: *Anigozanthos* hybrid cultivar Rambodiam.

Parentage:

*Parent.*—'Bush Pearl', not patented.

Propagation:

*Type.*—In vitro propagation of micro-plants.

*Time to initiate roots, summer.*—About 7 to 10 days at a temperature of approximately 25° C.

*Time to initiate roots, winter.*—About two weeks at a temperature of approximately 15° C.

*Time to produce a rooted young plant, summer.*—About 45 to 60 days at a temperature of approximately 25° C.

*Time to produce a rooted young plant, winter.*—About 55 to 70 days at a temperature of approximately 15° C.

*Root description.*—Fibrous, freely branching and white in color.

*Rooting habit.*—Freely branching.

Plant description:

*Plant and growth habit.*—Inverted triangle; compact, upright and outwardly spreading plant habit with branched flowering stems with predominately white-colored flowers. Moderately vigorous growth habit similar to the variety 'Bush Pearl'.

*Plant height.*—Average plant height including the inflorescence is about 55 cm (range 50 to 60 cm). Average height of foliage only is 30 cm (range 25 to 35 cm).

*Plant diameter.*—Average plant spread of a mature plant grown in 20 cm nursery pots or field plots in Tuggerah, New South Wales, Australia is 35 cm (observed summer 2007 through 2008).

*Lateral branch.*—Quantity per plant: About 20. Strength: Strong. Diameter: About 2 cm. Length of central internode: Approximately 3 mm. Texture: Smooth, glabrous. Color: 145B.

Foliage description:

*General description.*—The leaf attitude is erect to semi-erect and the degree of leaf curvature is slightly curved. Arrangement: Alternate equitant, simple; sessile.

*Leaves.*—Length: About 15 to 25 cm in a 14 cm pot. Width: About 10 to 12 mm in a 14 cm pot. Shape: Linear-slightly falcate. Apex: Acute. Base: Cauline. Margin: Entire. Texture, upper and lower surfaces: Smooth, glabrous; weak glaucosity and sparsely pubescent on leaf margin. Venation pattern: Parallel. Color of the upper and lower surfaces: 147A with indistinguishable venation (observed spring 2006).

Flower description:

*General description.*—Flowers arranged singly on terminal and axillary racemes. Flowers with tubular perianth; zygomorphic. Terminal flowers are held upright and attitude of flowers gradually changes to a horizontal position proximally. The proximal flowers are the first to open and usually are the only flowers to express perianth lobe reflexure. Flowers not fragrant. Flowers persistent. The length of the lowest inflorescence branch including raceme: About 10 to 12 cm. Number of flowers per inflorescence: About 2 racemes per inflorescence, each with about 20 flowers greater in length than 3 mm in a 14 cm pot (observed summer 2007 through 2008). Inflorescence height: About 50 cm. Inflorescence diameter: About 14 to 15 cm. Flower diameter: About 4 to 5 mm measured at the base of the lobes and about 2.2 cm across the lobes on an opened flower. Flower height: About 5 mm measured at base of perianth lobes and about 9 mm across the lobes on an opened flower.

*Natural flowering season.*—'Rambodiam' flowers almost continuously under outdoor growing conditions.

*Bud just before opening.*—Shape: Tubular. Length: About 3.5 cm. Width: About 5 mm. Texture: Tomentose. Color: 144A with dense pubescence colored NN155B with tips of these hairs colored ranging from 59C to 59D.

*Perianth.*—Arrangement: Fused elongated tube with six weakly reflexed acute lobes; split on lower surface. Appearance: Parallel to broadening evenly. Perianth tube length: About 3.5 to 4.0 cm. Perianth tube diameter: About 5 mm; at base, about 6 mm. Lobe length: About 1.0 cm. Lobe width: About 5 mm at base. Texture, outer surface of perianth tube: Tomentose. Texture, inner surface of perianth tube: Smooth, glabrous. Color: When opening and fully opened, outer surface of perianth tube: NN155B. When opening and fully opened, inner surface of perianth tube: 144B.

*Floral bracts.*—Length: up to 7 cm. Width: About 6 mm at base. Shape: Ensiform tapering to a narrow conduplicate form at the apex. Apex: narrow acute. Base: Clasping. Margin: Entire. Texture, upper surface: Smooth, glabrous. Texture, lower surface: Tomentose. Color, upper surface: 137B. Color, lower surface: 137B.

*Peduncle* (*flowering stems*).—Strength: Strong, stout. Aspect: Upright to outwardly spreading. Length: About 40 to 45 cm. Diameter at base: About 8.0 mm. Texture: Tomentose. Color of surface: 146B. Pubescence color: Ranging from 59A to 59B with color of hairs at junction with floral bracts NN155B with reddening of hair tips absent at this point.

*Pedicels* (*individual flower stems*).—Length: About 3 mm. Diameter: About 2 mm. Angle: Distally appressed to flowering stems, then about 30° to 45° from flowering stems proximally with the largest, most mature flowers. Strength: Strong. Texture: Tomentose. Color: 144A. Pubescence color: Middle third of hairs on the pedicel is NN155B with tips of these hairs having a color of 59C to 59D.

*Reproductive organs.*—Stamens: Quantity: 6 per flower. Anther shape: Oblong. Anther size: About 1 mm by 3 mm. Anther color: 12B. Pollen amount: Scarce. Pollen color: 12B. Pistils: Quantity: One per flower. Pistil length: About 3 cm. The position of the stigma in relation to the anthers is level. Style length: About 2.8 cm. Style color: 145A. Stigma shape: Rounded. Stigma color: 144A. Ovary color: 144A with pubescence of NN155B with tips of hairs colored ranging from 59C to 59D.

Seed and fruit production: Seed and fruit development have not been observed on plants of the new *Anigozanthos.*

Environmental tolerances: 'Rambodiam' plants have exhibited good tolerance to rain and wind and to tolerate temperatures from 1 to about 40° C. 'Rambodiam' has moderate to good drought tolerance. 'Rambodiam' has moderate to good recovery with watering after severe wilting. 'Rambodiam' does well in sandy and gravelly soils.

Disease resistance: 'Rambodiam' has not been observed to be resistant to other pathogens and pests common to *Anigozanthos.* It is expected that resistance to common *Anigozanthos* diseases such as rust are similar to the parent 'Bush Pearl'.

What is claimed is:

1. A new and distinct variety of *Anigozanthos* hybrid plant named 'Rambodiam', substantially as herein shown and described.

* * * * *